United States Patent [19]
Nakamura et al.

[11] Patent Number: 5,325,135
[45] Date of Patent: Jun. 28, 1994

[54] OPHTHALMOLOGIC APPARATUS HAVING TWO MEASURING SYSTEMS

[75] Inventors: Yukitsugu Nakamura, Sagamihara; Haruhisa Madate; Takashi Masuda, both of Kawasaki, all of Japan

[73] Assignee: Canon Kabushiki Kaisha, Tokyo, Japan

[21] Appl. No.: 126,095

[22] Filed: Aug. 19, 1993

Related U.S. Application Data

[63] Continuation of Ser. No. 663,066, Mar. 1, 1991, abandoned, which is a continuation of Ser. No. 536,089, Jun. 11, 1990, abandoned, which is a continuation of Ser. No. 430,933, Nov. 19, 1989, abandoned, which is a continuation of Ser. No. 162,250, Feb. 19, 1988, abandoned.

[30] Foreign Application Priority Data

| Mar. 6, 1987 | [JP] | Japan | 051785 |
| Mar. 16, 1987 | [JP] | Japan | 058286 |
| May 30, 1987 | [JP] | Japan | 135634 |
| May 30, 1987 | [JP] | Japan | 135635 |

[51] Int. Cl.$^5$ ............................................. A61B 3/10
[52] U.S. Cl. .................................. 351/212; 351/205; 351/211
[58] Field of Search ............... 351/205, 211, 214, 212; 128/303.1, 76.5, 645, 648, 652; 606/4, 5, 6, 204.25

[56] References Cited

U.S. PATENT DOCUMENTS

| 2,999,422 | 9/1961 | Papritz | 351/214 |
| 3,070,997 | 1/1963 | Papritz | 351/214 |
| 3,453,998 | 7/1969 | Giglio . | |

Primary Examiner—William L. Sikes
Assistant Examiner—Hung X. Dang
Attorney, Agent, or Firm—Fitzpatrick, Cella, Harper & Scinto

[57] ABSTRACT

An apparatus capable of simply and accurately measuring cornea refractive power and eye axis length at least necessary to select a proper in-the-eye lens for an eye to be examined without moving a slidable bed in a horizontal plane.

40 Claims, 8 Drawing Sheets

OPHTHALMOLOGIC APPARATUS HAVING TWO MEASURING SYSTEMS

This application is a continuation of application Ser. No. 07/663,066 filed Mar. 1, 1991, now abandoned, which is a continuation of application Ser. No. 07/536,089 filed Jun. 11, 1990, now abandoned, which is a continuation of application Ser. No. 07/430,933 filed Nov. 2, 1989, now abandoned, which is a continuation of application Ser. No. 07/162,250 filed Feb. 29, 1988, now abandoned.

BACKGROUND OF THE INVENTION

1. Field of the Invention

This invention relates to an ophthalmologic apparatus having a plurality of measuring and examining functions of different working distances, such as an apparatus in which the function of measuring cornea refractive power and the function of measuring eye axis length are compounded.

2. Related Background Art

Heretofore, a spectacle lens or a contact lens has been used for the reform of the refractive power after the surgical operation of cataract, but in recent years, it has been the practiced to insert an in-the-eye lens into the position of the removed crystalline lens. To choose a proper in-the-eye lens for a patient having an eye without the crystalline lens, it is necessary to know the cornea refractive power and the eye axis length, i.e., the length from the cornea to the retina.

In the past, however, there has been the inconvenience that the measurement of the cornea refractive power is effected by a cornea shape measuring apparatus and the measurement of the eye axis length is effected by a discrete ultrasonic measuring apparatus, whereafter the refractive power of the in-the-eye lens must be calculated.

An apparatus having both functions is proposed in U.S. application Ser. No. 906,271 now U.S. Pat. No. 4,764,006. In this case, it is desired that during the measurement of the shape of the cornea, the corneal reflection image be not eclipsed by the image of an eye axis length measuring probe which is present in the optical path.

It is also desirable to eliminate the necessity that the system for measuring the eye axis length be optically transparent.

Further, an apparatus in which a slidable bed need not be moved in a horizontal plane is desirable because an attempt to effect two measurements by moving the slidable bed in a horizontal plane in the direction of the optic axis results in the destruction of the alignment in a direction perpendicular to the optic axis.

SUMMARY OF THE INVENTION

It is an object of the present invention to provide an ophthalmologic apparatus which can accomplish the measurement of the cornea refractive power and the measurement of the eye axis length with a slidable bed remaining fixed in a horizontal plane.

It is also an object of the present invention to provide an ophthalmologic apparatus in which during the measurement of the shape of the cornea, an eye axis length measuring probe does not adversely affect the measurement.

It is a further object of the present invention to provide an ophthalmologic apparatus in which during the measurement of the eye axis length, the positional relation between an eye axis length measuring probe and an eye to be examined can be observed.

It is still a further object of the present invention to provide an ophthalmologic apparatus in which both during the measurement of the cornea refractive power and during the measurement of the eye axis length, the front eye part can be observed through a common monitor.

DESCRIPTION OF THE PREFERRED EMBODIMENTS

Figure 1:
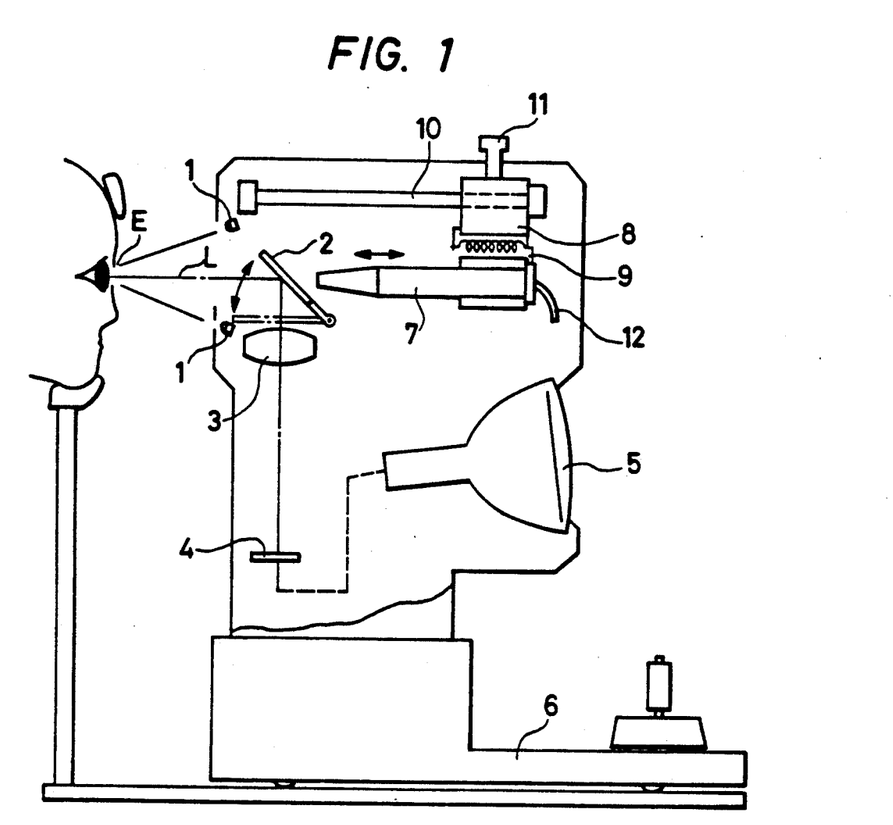
FIGS. 1 to 3 illustrate a first embodiment of the present invention.
Figures 2, 3:
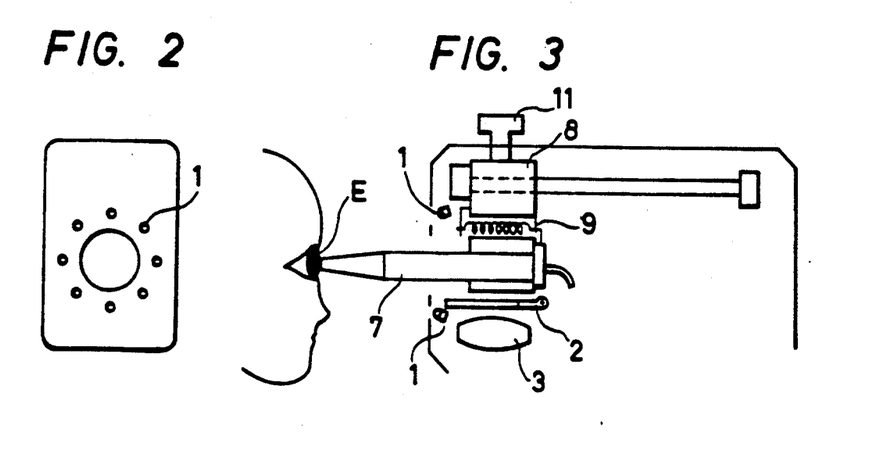

Referring to FIGS. 1 to 3 which show an embodiment of the present invention, a first measuring system for measuring the refractive power of the cornea of an eye E to be examined and a second measuring system for finding the eye axis length of the eye E to be examined are provided in a main body supported by a slidable bed.

The first measuring system for measuring the refractive power of the cornea is comprised of a projection index light source 1, a movable mirror 2, an objective lens 3 and a two-dimensional image pickup element 4. The projection index light source 1 comprises a plurality of light-emitting diodes disposed on a circumference about a measurement optic axis L as shown, for example, in FIG. 2, and is projected onto the cornea of the eye E to be examined with a prescribed spatial distance provided therebetween. Thereupon, the corneal reflection image of the projection index light source 1 is formed by the convex mirror action of the cornea, and since the shape of the corneal reflection image varies in conformity with the magnitudes of the radius of curvature and the degree of astigmatism of the cornea, it is possible to find the refractive power of the cornea, the degree of astigmatism of the cornea and the axis angle of the cornea by detecting said variation, as is well known.

In the present embodiment, as previously described, the detection is accomplished by causing the corneal reflection image of the projection index light source 1 to be formed on the two-dimensional image pickup element 4 by the objective lens 3 through the movable mirror 2. The detection signal is signal-processed by an electric circuit, not shown, and is further operation-processed to thereby find the refractive power of the cornea, the degree of astigmatism of the cornea and the axis angle of the cornea. The two-dimensional image pickup element 4 is designed such that it can be utilized not only for the detection of the measuring signal but also for the observation of the front eye part of the eye E to be examined and can be aligned by operating a well-known slidable bed 6 while carrying out the observation of the front eye part by means of a TV monitor 5.

The second measuring system for measuring the eye axis length is comprised of a probe 7, a probe holder 8, a tension spring 9, a slidable guide member 10 and a slidable operating lever 11.

The probe 7 contains therein an ultrasonic oscillator and a receiver which are connected to an electric circuit portion, not shown, through a cable 12.

In the present embodiment, during the measurement of the refractive power of the cornea, the probe 7 is retracted rearwardly of the movable mirror 2 so as not to interfere with the cornea refractive power measuring optical path, but during the measurement of the eye axis length, as shown in FIG. 3, the movable mirror 2 is brought down and the probe 7 is protruded toward the eye E to be examined by the operation of sliding the slidable operating lever 11 forwardly. At this time, the slidable bed 6 is fixed (the slidable bed 6 may be more reliably fixed if the lock means of the slidable bed 6 is used), and the alignment need not be re-adjusted by the operation of the slidable operating lever 11. By finely aligning the slidable bed 6 as required, the tip end of the probe 7 can be brought into contact with the cornea of the eye E to be examined. The probe 7 is held by the probe holder 8 so as to be accurately slidable back and forth, i.e., in the direction of the measuring optic axis L, and also is biased forwardly by the weak tension spring 9. Therefore, even if the probe 7 is brought too close to the eye E to be examined, the probe 7 retreats against the weak force of the tension spring 9, whereby the end surface of the probe 7 is brought into contact with the cornea of the eye E to be examined with predetermined weak pressure so as not to forcibly dent the cornea or inflict any injury thereto.

With the probe 7 being brought into contact with the cornea of the eye to be examined, an ultrasonic wave pulse is oscillated from the tip end of the probe 7 and the reflected echo from the retina of the eye E to be examined is received, whereby the eye axis length from the surface of the cornea to the retina can be detected to find the measured value, as is well known.

It is also well known that after the refractive power of the cornea of the eye E to be examined and the eye axis length have been measured in the manner described above, the refractive power of an artificial crystalline lens can be calculated by a calculation formula from which these values have been empirically obtained.

Figure 4:
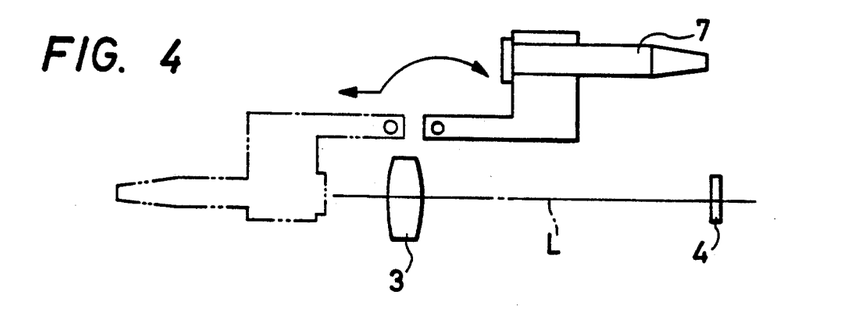
FIG. 4 illustrates a second embodiment of the present invention.

FIG. 4 shows a second embodiment of the present invention which is designed such that during the measurement of the refractive power of the cornea, the probe 7 for measuring the eye axis length is raised above the objective lens 3 and that when the eye axis length is to be measured, the probe 7 is rotated forwardly as indicated by arrow and further the probe 7 is protruded forwardly with the slidable bed 6 remaining fixed, whereby the probe is brought close to the cornea of the eye E to be examined.

Figure 5:
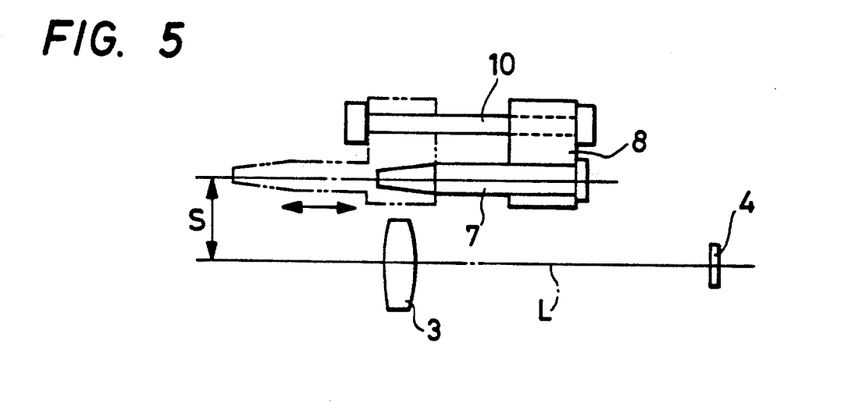
FIG. 5 illustrates a third embodiment of the present invention.

FIG. 5 shows a third embodiment of the present invention in which the measuring optic axis L of the measuring system for measuring the refractive power of the cornea is not coincident (is parallel-eccentric) with the center axis of the probe 7 of the measuring system for measuring the eye axis length. The probe 7 of the measuring system for measuring the eye axis length is disposed above the measuring optic axis L of the measuring system for measuring the refractive power of the cornea, and the probe 7 is held by the probe holder 8 in a manner similar to the first embodiment, and when the eye axis length is to be measured, the probe 7 may be displaced by S in a plane perpendicular to the optic axis to bring the center axis of the probe 7 into coincidence with the measuring optic axis L and the probe 7 may be moved along the slidable guide member 10 toward the eye to be examined, and when the refractive power of the cornea is to be measured, the probe 7 may be retracted rearwardly.

In the present embodiment, when the eye axis length is to be measured after the refractive power of the cornea has been measured, it is necessary to re-adjust the height of the measuring portion (for example, to displace the slidable bed 6 by S in a plane perpendicular to the optic axis), but this embodiment has an advantage of simpler structure.

A fourth embodiment of the present invention will now be described.

Figure 6:
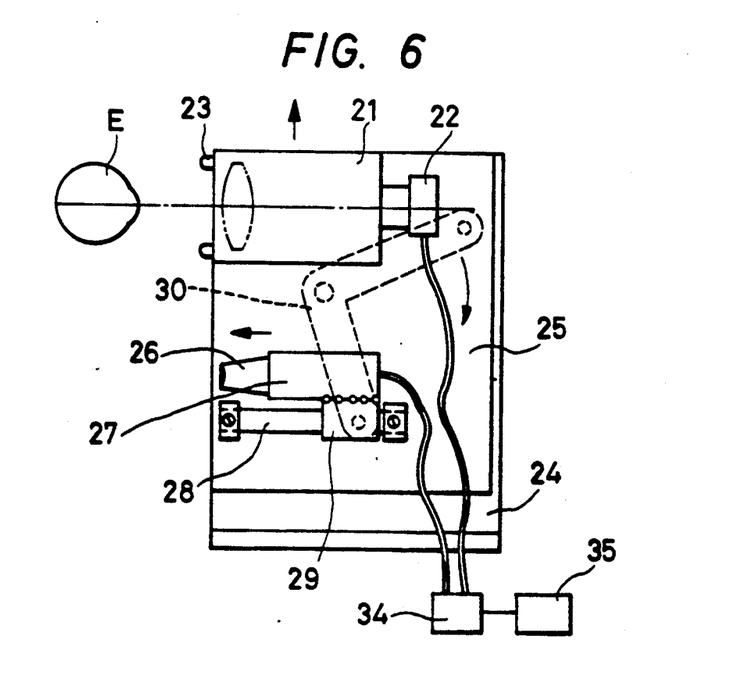
FIG. 6 shows a mechanism as seen from a side in a fourth embodiment of the present invention.
Figure 7:
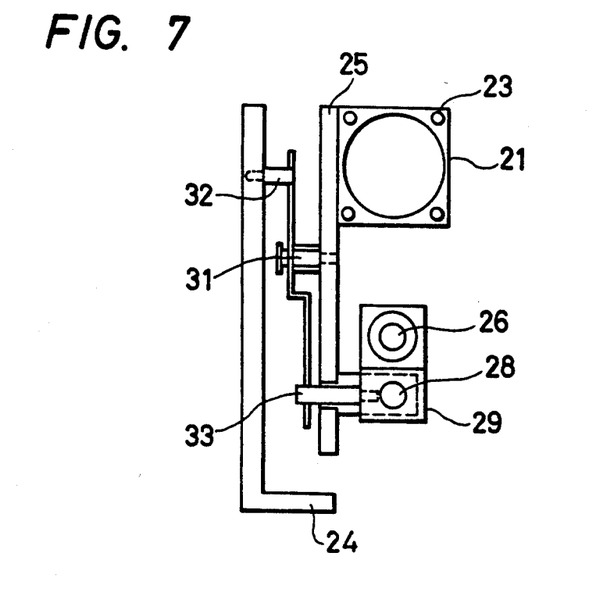
FIG. 7 is a front view of the mechanism.
Figure 8:
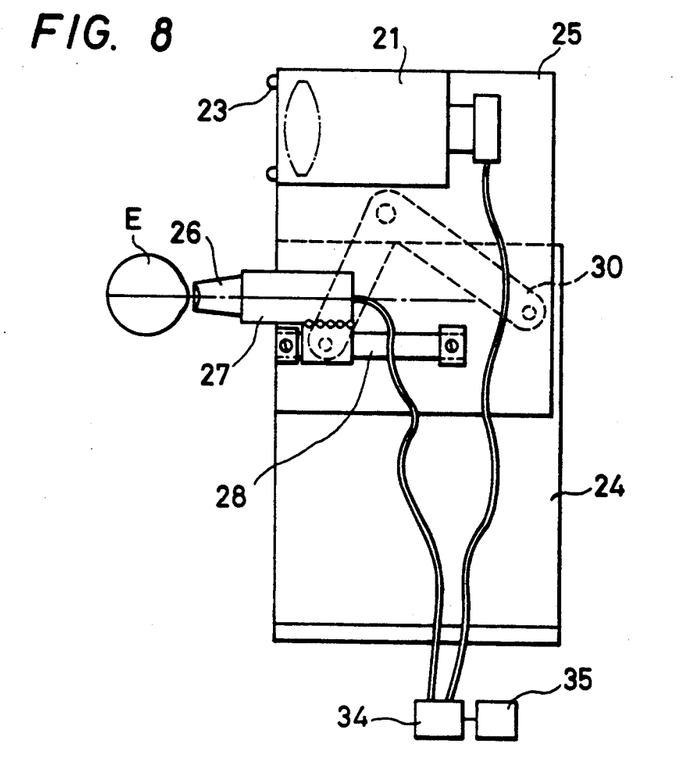
FIG. 8 shows the mechanism during the measurement of the eye axis length.

FIG. 6 is a side view of the mechanism, and FIG. 7 is a front view of the mechanism. A cornea curvature measuring optical system 21 is disposed in opposed relationship with an eye E to be examined, a light-receiving device 22 is provided rearwardly thereof, and a plurality of light sources 23 disposed circumferentially are provided on the front portion of the cornea curvature measuring optical system 21. The cornea curvature measuring optical system 21 and the light-receiving device 22 are mounted in a movable portion 25 positioned on a fixed portion 24. An eye axis length detector 26 is provided below the cornea curvature measuring optical system 21, and an eye axis length optical system 27 is disposed rearwardly of the eye axis length detector 26 and is fixed to a boss 29 movable back and forth in a horizontal direction along a guide bar 28. The eye axis length optical system 27, etc. are raised upwardly by an interlocking arm 30 and is adapted to protrude toward the eye E to be examined with this movement. The interlocking arm 30 is pivotally mounted on the movable portion 25 by a pin 31 and on the fixed portion 24 by a pin 32. The boss 29 is fixed to the interlocking arm 30 through a pin 33, and when the movable portion 25 is moved vertically upwardly, the eye axis length detector 26 is moved also in a horizontal direction and is set to a measuring condition in opposed relationship with the eye E to be examined as shown in FIG. 8. The signals from the light-receiving device 23 and the eye axis length detector 26 are processed by an operation processing circuit 34, and the refractive power of the lens in the eye may be displayed on a display unit 35.

Figure 9:
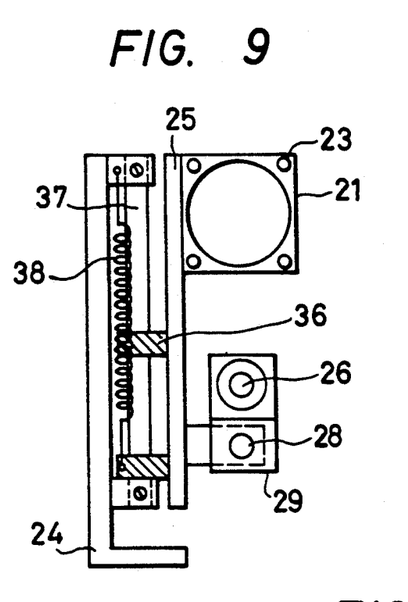
FIG. 9 shows the connection between a movable portion and a fixed portion.

FIG. 9 shows the connection between the movable portion 25 and the fixed portion 24. A boss 36 fixed to the movable portion 25 fits to a sliding shaft 37 fixed to the fixed portion 24 and moves vertically so that the weights of the movable portion 25 and the optical system are negated by a balance spring 38.

Figure 10:
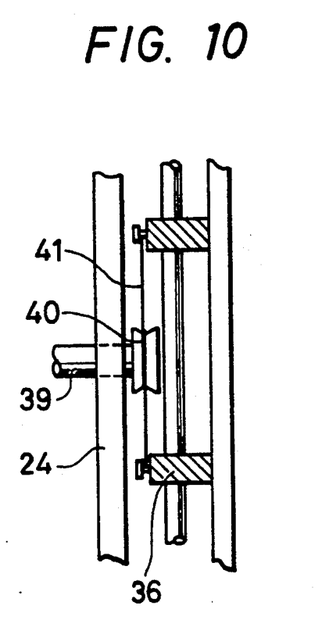
FIG. 10 shows a vertically moving mechanism portion.

FIG. 10 shows a mechanism for vertically moving the movable portion 25. When a vertically moving shaft 39 supported by the fixed portion 24 is rotated, the movable portion 25 may be moved vertically by a wire 41 wound on a pulley 40, journalled to the vertically moving shaft 39, and fixed to the boss 36.

Figure 11:
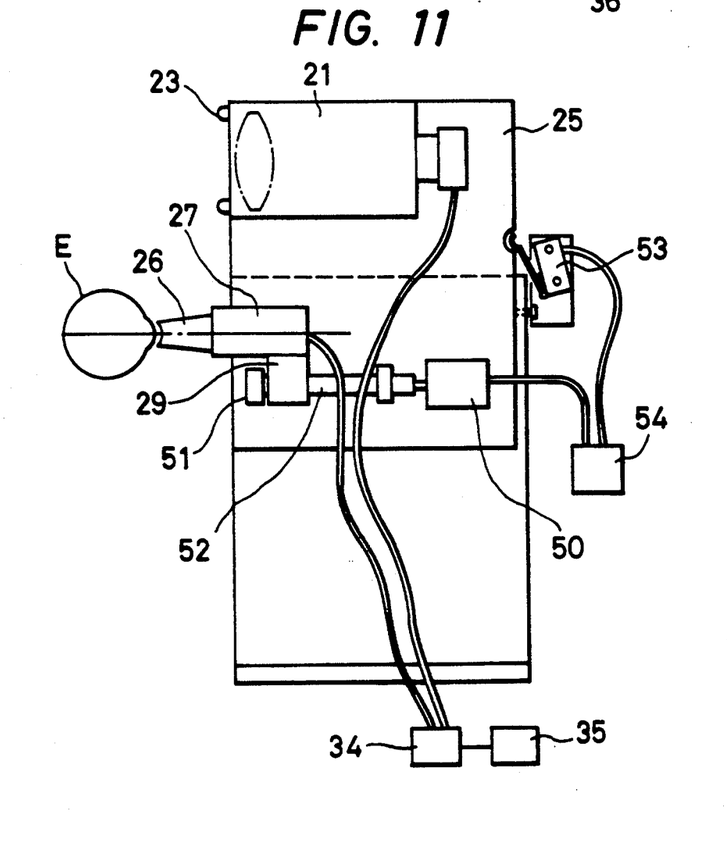
FIG. 11 shows the mechanism of a fifth embodiment of the present invention.

In the fourth embodiment, the vertical movement of the movable portion 25 and the horizontal movement of the eye axis length detecting portion 27 are mechanically connected together, but alternatively, these movements can be electrically accomplished, and FIG. 11 shows a fifth embodiment of the present invention in which the interlocking mechanism is electrical. In this embodiment, a boss 29 is threadably engaged with a screw bar 52 rotated by an electric motor 50 and supported by a supporting portion 51, and the movement of the movable portion 25 may be detected by a microswitch 53. The output of the microswitch 53 is connected to an electric motor control circuit 54 so that the electric motor 50 may be operated by the direction of the control circuit 54.

In the fifth embodiment, when the movable portion 25 is moved upwardly and the microswitch 53 detects a predetermined position of the movable portion 25, the electric motor 50 rotates the screw bar 52 in a direction to feed the eye axis length detector 27 horizontally forwardly and the boss 29 bears against the supporting portion 51, and when an overload current flows to the electric motor 50, the rotation of the electric motor 50 is stopped by the electric motor control circuit 54. When the movable portion 25 is moved downwardly, the microswitch 53 detects it and puts out a signal for reversely rotating the electric motor 50 by the control circuit 54, and the eye axis length detector 26 is moved away from the eye E to be examined.

Figure 12A:
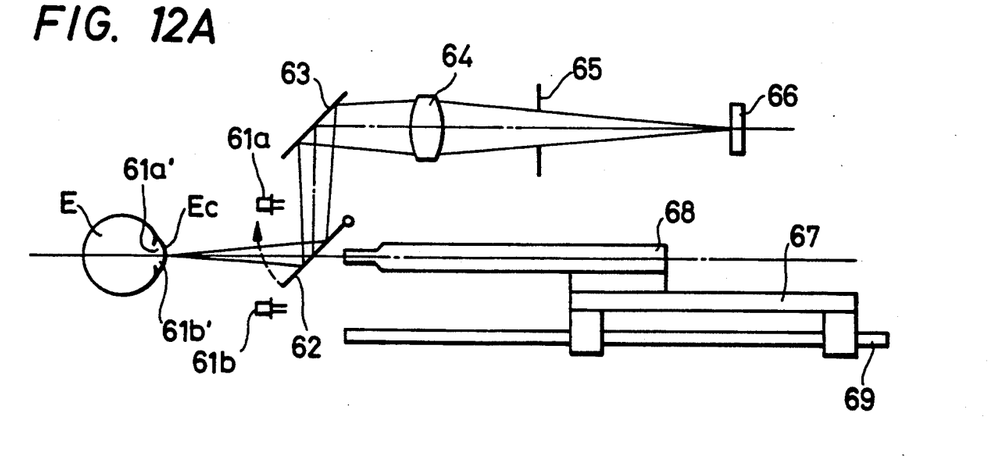
FIGS. 12A and 12B show a sixth embodiment of the present invention, FIG. 12A representing the state during the measurement of the shape of the cornea, and FIG. 12B representing the state during the measurement of the eye axis length.
Figure 12B:
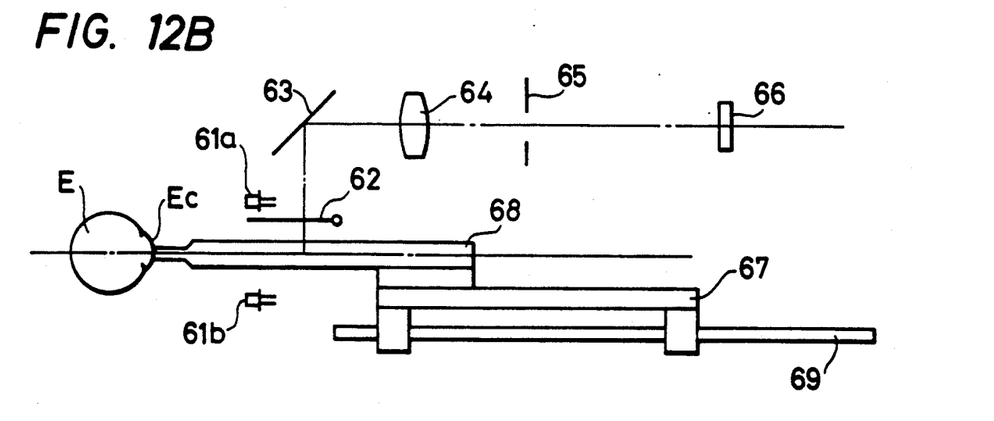

FIGS. 12A and 12B show a sixth embodiment of the present invention, FIG. 12A representing a state in which the shape of the cornea is being measured, and FIG. 12B representing a state in which the eye axis length is being measured. Designated by 61a–61d (61c and 61d being not shown in FIG. 12) are LEDs used as light sources for illuminating the eye E to be examined. A jump-up mirror 62 is provided forwardly of the eye E to be examined, a mirror 63 is disposed in the direction of reflection thereof, and an imaging lens 64, a stop 65 and an image pickup element 66 are arranged in succession in the direction of reflection of the mirror 63. In front of the eye E to be examined behind the jump-up mirror 62, an ultrasonic measuring probe 68 for measuring the eye axis length or the like supported by a probe holder 67 is disposed for movement back and forth along a slidable guide member 69.

When the shape of the cornea is to be measured, the jump-up mirror 62 is lowered into the optical path as shown in FIG. 12A and the reflected images 61a–61d by the cornea Ec of the eye E to be examined are reflected by the jump-up mirror 62 and the mirror 63 and are formed on the image pickup element 66 through the imaging lens 64 and the stop 65.

Figure 13:
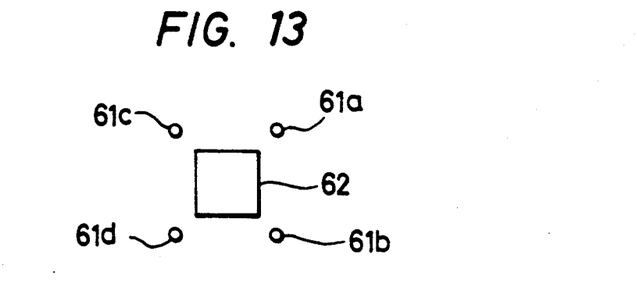
FIG. 13 shows the arrangement relation between light sources and a jump-up mirror.

FIG. 13 shows the arrangement relation between the light sources 61a–61d and the jump-up mirror 62. The light sources 61a–61d are disposed at equal intervals on two meridians orthogonal to each other. The stop 65 compensates for the variations in the sizes of the corneal reflection images 61a'–61d' by the error for the distance between the entire apparatus and the eye E to be examined. In addition to a method of finding the radii of curvature and the angles on the strongest principal meridian and the weakest principal meridian from three coordinate positions on the two meridians orthogonal to each other in order to calculate the shape of the cornea from the corneal reflection images 61a'–61d', a known method may be resorted to.

Figure 14:
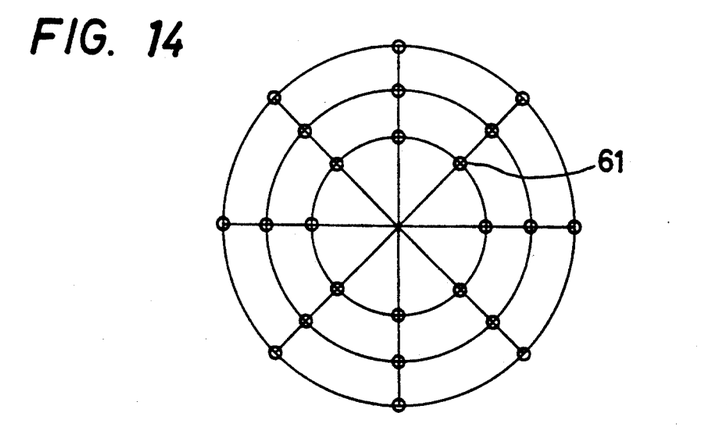
FIG. 14 shows another arrangement of light sources.

Also, as shown in FIG. 14, the shape of the cornea can be measured at higher accuracy by the measurement on two or more sets of meridians, and it is also easy to dispose the light sources 61 on the circumferences of a plurality of concentric circles and calculate the measured values on different regions on the cornea Ec.

When for example, the eye axis length is to be measured, the jump-up mirror 62 is removed from the optical path opposed to the cornea Ec of the eye E to be examined as shown in FIG. 12B, and in the response thereto, the probe holder 67 and the ultrasonic measuring probe 68 slide on the slidable guide member 69 and move to a position in which it is in contact with or proximate to the cornea Ec of the eye E to be examined. Thus, measurement of the shape of the cornea and measurement of the eye axis length can be accomplished without moving the entire apparatus. Also, the measuring probe 68 is biased forwardly by a sliding mechanism of low friction force between it and the probe holder 67 with the aid of a weak tension spring or the like, not shown, and even when the entire apparatus is brought too close to the eye E to be examined, the measuring probe 68 retreats and does not forcibly apply a force to the cornea Ec, thus preventing a damage from being imparted to the cornea Ec or the eye axis length from being measured short. A known method is used to calculate the refractive power of the artificial crystalline lens from such measured values of the shape of the cornea and the eye axis length.

Figure 15:
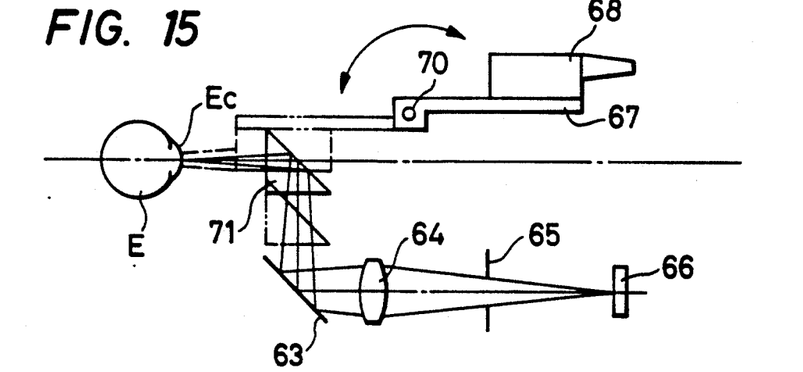
FIG. 15 shows the construction of a seventh embodiment of the present invention.

FIG. 15 shows a seventh embodiment of the present invention. In FIG. 15, the portions indicated by solid lines show the arrangement during the measurement of the shape of the cornea, and are moved as indicated by broken lines during the measurement of the eve axis length. The reference numeral 70 designates the center of rotation of a probe holder 67, and in response to the downward movement of a prism 71 used instead of the jump-up mirror 62 of FIG. 12 as indicated by broken line, a measuring probe 68 is rotated so as to be proximate to or in contact with the cornea Ec of the eye E to be examined.

Figure 16:
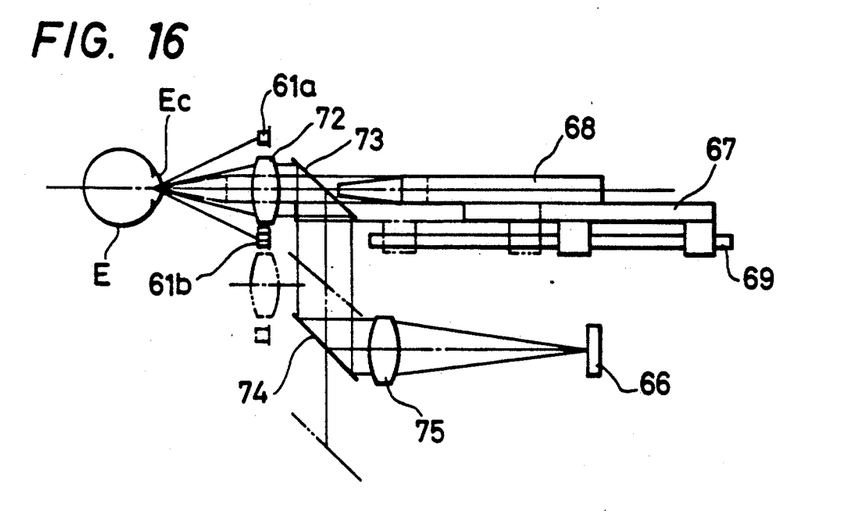
FIG. 16 shows the construction of an eighth embodiment of the present invention.

FIG. 16 shows an eighth embodiment of the present invention. In FIG. 16, the solid lines represent the state during the measurement of the shape of the cornea, and the broken lines represent the state during the measurement of the eye axis length. In the case of the measurement of the shape of the cornea, the corneal reflection images 61a'-61d' of light sources 61a-61d are made into a substantially parallel light by an objective lens 72 opposed to the eye E to be examined, and this light is reflected by mirrors 73 and 74 and imaged on the image pickup element 66 by a relay lens 75.

In the case of the measurement of the eye axis length, the objective lens 72 and the mirrors 73 and 74 are moved downwardly and also the probe holder 67 and the measuring probe 68 are moved on the slidable guide member 69 so as to be proximate to or in contact with the cornea Ec of the eye E to be examined, thereby effecting the measurement.

Figure 17A:
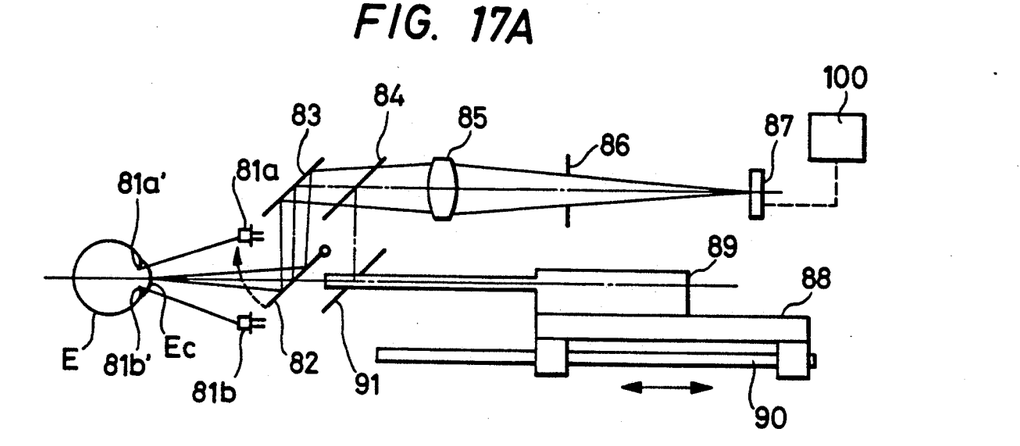
FIGS. 17A and 17B show a ninth embodiment of the present invention, FIG. 17A representing the state during the measurement of the shape of the cornea, and FIG. 17B representing the state during the measurement of the eye axis length.
Figure 17B:
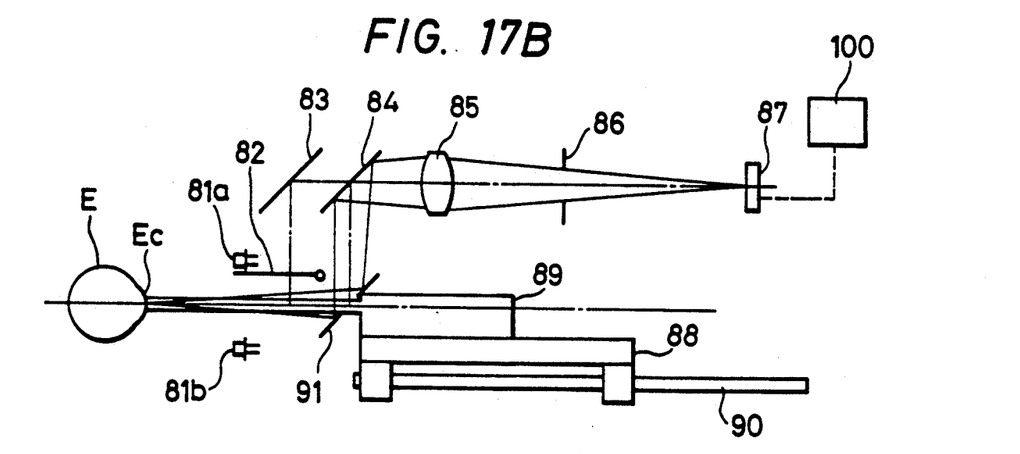

FIGS. 17A and 17B show a ninth embodiment of the present invention, FIG. 17A representing the state in which the shape of the cornea is being measured, and FIG. 17B representing the state in which the eye axis length is being measured. Designated by 81a-81d (81c and 81d being not shown in FIG. 17) are LEDs used as light sources for illuminating the eye E to be examined. A jump-up mirror 82 is provided forwardly of the eye E to be examined, a mirror 83 is disposed in the direction of reflection thereof, and an obliquely disposed half-mirror 84, an imaging lens 85, a stop 86 and an image pickup element 87 are arranged in succession in the direction of reflection of the mirror 83. In front of the eye E to be examined behind the jump-up mirror 82, an ultrasonic measuring probe 89 supported by a probe holder 88 is disposed for movement back and forth along a slidable guide member 90. A mirror 91 having a hole at the center thereof and disposed obliquely is fixed around the ultrasonic measuring probe 89, and the measuring probe 89 is movable back and forth through this mirror 91.

When the shape of the cornea is to be measured, the jump-up mirror 82 is lowered as shown in FIG. 17A and light beams emitted from the light sources 81a-81d are reflected by the cornea Ec of the eye E to be examined and form reflected images 81a'-81d' and are further reflected by the jump-up mirror 82 and the mirror 83 and are transmitted through the half-mirror 84, whereafter they are condensed by the imaging lens 85, pass through the stop 86 and are imaged on the image pickup element 87. The image pickup element 87 can be utilized not only for the detection of the measuring signal but also for the observation of the front eye part of the eye E to be examined and can accomplish alignment while effecting the observation of the front eye part by a TV monitor 100.

Figure 18:
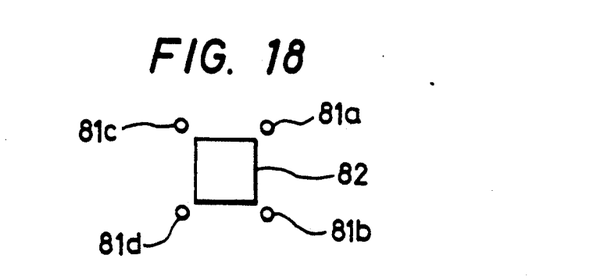
FIG. 18 shows an arrangement of a jump-up mirror and light sources.

FIG. 18 shows the positional relation between the light sources 81a-81d and the jump-up mirror 82. The light sources 81a-81d are arranged at equal intervals on two meridians orthogonal to each other. The stop 86 compensates for the variations in the sizes of the corneal reflection images 81a'-81d' by the error for the distance between the entire apparatus and the eye E to be examined. To calculate the shape of the cornea from the optical images formed on the image pickup element 87, a known method may be resorted to besides a method of finding the radii of curvature and the angles on the strongest principal meridian and the weakest principal meridian from three or more coordinates positions on two meridians orthogonal to each other.

Figure 19:
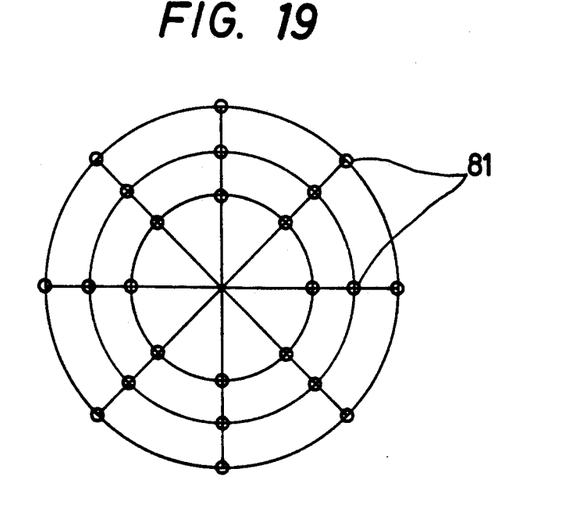
FIG. 19 shows another arrangement of light sources.

Also, more accurate measurement of the shape of the cornea is possible by the measurement on two or more sets of meridians as shown in FIG. 19, and it is also easy to dispose light sources 81 on the circumferences of a plurality of concentric circles and calculate the measured values at different regions on the cornea Ec.

During the measurement of the eye axis length, as shown in FIG. 17B, the jump-up mirror 82 is removed from the optical path opposed to the cornea Ec of the eye E to be examined, and in response thereto, the probe holder 88 and the measuring probe 89 slide on the slidable guide member 90 and move to a position in which they are in contact with or proximate to the cornea Ec of the eye E to be examined. At this time, the positional relation between the eye E to be examined and the eye axis length measuring probe 89 is also observed by means of an observation optical system. That is, the light beams emitted from the light sources 81 are reflected on the cornea Ec, are reflected by the mirror 91 and the half-mirror 84 around the eye axis length measuring probe 89, are condensed by the imaging lens 85, pass through the stop 86 and are imaged on the image pickup element 87.

If the output signal from this image pickup element 87 is made into an image by the use of the monitor 100 through an image processing circuit, not shown, the dispositions and states of the eye axis length measuring probe 89 and the front eye part of the eye E to be examined can be observed and therefore, fine position adjustment of the eye axis length measuring probe 89 can be accomplished and the measurement accuracy is improved. When the entire apparatus has been brought too close to the eye E to be examined, the eye axis length measuring probe 89 is slid on the probe holder 88 by a slidable portion provided between the eye axis length measuring probe 89 and the probe holder 88 and movable with a low friction force and an unshown spring urging the eye axis length measuring probe 89 toward the cornea Ec with a very weak force, thereby preventing the cornea Ec from being deformed and preventing the eye axis length from being measured shorter than actually. Further, in this case, the image of the tip end portion of the eye axis length measuring probe 89 displayed on the monitor by the aforementioned observation optical system moves or is blurred and thus, the examiner can know on the spot that the eye axis length measuring probe 89 has contacted the cornea Ec. To calculate, for example, the refractive power of the artificial crystalline lens from the measured values of the shape of the cornea and the eye axis length obtained by means of such an apparatus, use may be made of a known method.

Figure 20:
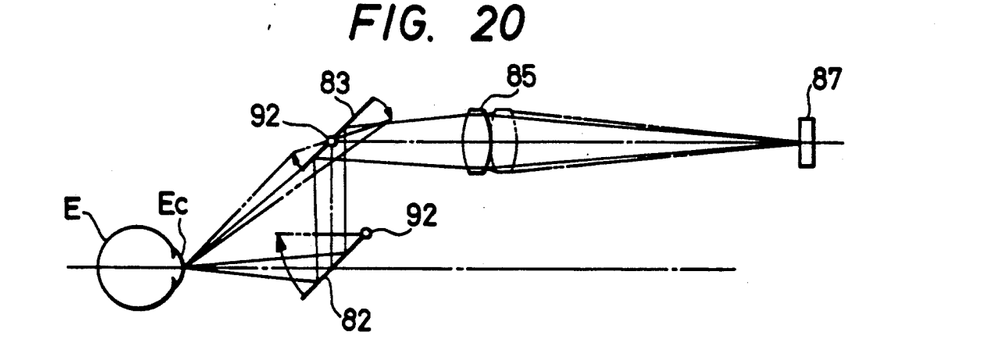
FIG. 20 shows the construction of a tenth embodiment of the present invention.

FIG. 20 shows a tenth embodiment of the present invention. In this embodiment, the jump-up mirror 82 and the mirror 83 operate in association with each other, and during the measurement of the cornea, they provide an optical system similar to that of FIG. 17A as depicted by solid lines, and the corneal reflection images 81a'-81d' of the light sources 81a-81d are formed on the image pickup element 87.

During the measurement of the eye axis length, the jump-up mirror 82 jumps up as indicated by broken line and at the same time, the mirror 83 is rotated by a predetermined angle about the center of rotation 92, and as in FIG. 17B, the eye axis length measuring probe 89, not shown, is moved toward the eye E to be examined and further, the imaging lens 85 is also moved to a broken-line position to thereby place the probe tip end portion and the image pickup element 87 in a conjugate relation. Again in this case, the observation of the front eye part of the eye E to be examined and the probe tip end portion can be accomplished, and this is convenient for measurement as in the case of FIG. 17.

Figure 21:
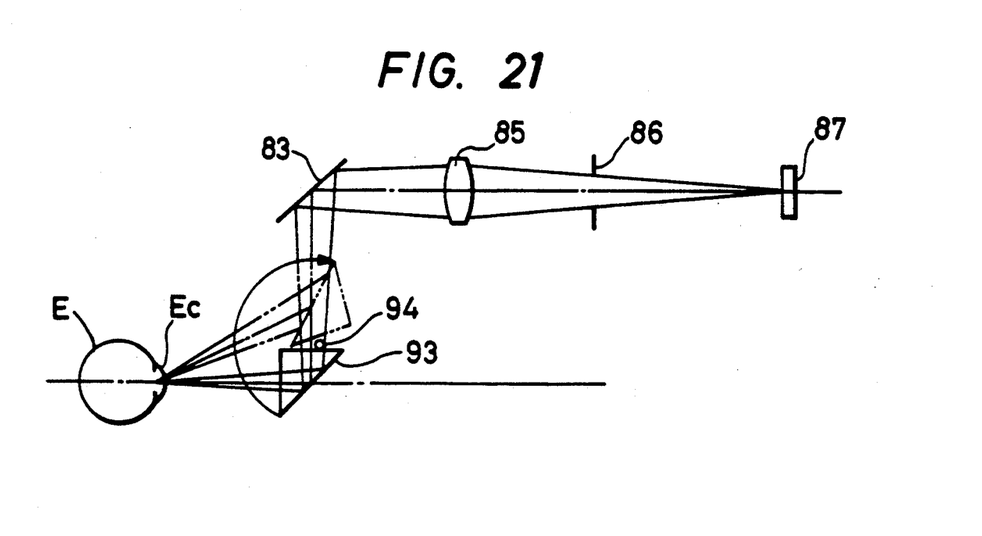
FIG. 21 shows the construction of an eleventh embodiment of the present invention.

FIG. 21 shows an eleventh embodiment of the present invention. In FIG. 21, the solid lines represent the state during the measurement of the shape of the cornea, and the broken lines represent the state during the measurement of the eye axis length. In this embodiment, a prism 93 is installed instead of the jump-up mirror 82 in FIGS. 17A and 17B, and during the measurement of the eye axis length, the prism 93 may be rotated by a predetermined angle about the center of rotation 94 to thereby form an observation optical system. Also, by suitably selecting the refractive index of the prism 93, it is also possible to correct the difference between the length of the optical path during the measurement of the shape of the cornea and the length of the optical path during the measurement of the eye axis length.

We claim:

1. An ophthalmologic apparatus, comprising:
    a frame for measuring systems;
    a first measuring system, disposed in said frame for effecting a calculation of first information of an eye to be examined at a predetermined working distance relative to the eye to be examined, said frame being supported by a slidable bed, said first measuring system effecting the calculation when said frame and the eye to be examined are aligned with each other by moving the slidable bed;
    a second measuring system, disposed in said frame, said second measuring system including a measuring terminal for effecting a calculation of second information of the eye to be examined when said measuring terminal is brought into contact with the eye to be examined; and
    guiding means for linearly sliding said measuring terminal of said second measuring system relative to said frame aligned with the eye to be examined in the same direction as the optic axis of said first measuring system at least at positions directly before the eye to be examined without moving said slidable bed in the direction of the optic axis of said first measuring system when a change-over of said first measuring system and said second measuring system is performed.

2. An ophthalmologic apparatus according to claim 1, wherein said first measuring system is provided with an apertured mirror fixed in the optical path, and said measuring terminal is movable in the direction of the optic axis through the aperture of said apertured mirror.

3. An ophthalmologic apparatus according to claim 1, wherein said measuring terminal is biased toward the eye to be examined.

4. An ophthalmologic apparatus according to claim 1, further provided with an observation optical system through which the front eye part of the eye to be examined around said measuring terminal can be observed with said measuring terminal being in contact with the eye to be examined.

5. An ophthalmologic apparatus according to claim 4, wherein said observation optical system is provided with an optic axis forming a predetermined angle with respect to the direction of movement of said measuring terminal.

6. An ophthalmologic apparatus according to claim 4, wherein said observation optical system is provided with an optic axis coincident with the direction of movement of said measuring terminal.

7. An ophthalmologic apparatus according to claim 4, wherein said observation optical system and said first measuring system are provided with at least one common optical member.

8. An ophthalmologic apparatus according to claim 7, wherein said common optical member is a reflecting member, and the position of said reflecting member in said observation optical system is rotatably displaced relative to the position thereof in said first measuring system.

9. An ophthalmologic apparatus, comprising:
    a frame for measuring systems;
    a first detecting system, disposed in said frame for effecting the detection of first information of an eye to be examined at a predetermined working distance relative to the eye to be examined, said frame being supported by a slidable bed, said first detecting system effecting the calculation when said frame and the eye to be examined are aligned with each other by moving the slidable bed;
    a second detecting system, disposed in said frame, said second detecting system including a detecting terminal for effecting the detection of second information of the eye to be examined brought into contact with the eye to be examined; and
    movable means for moving said detecting terminal of said second detecting system relative to said frame aligned with the eye to be examined in the direction of the optic axis of said first detecting system at least at positions directly before the eye to be examined without moving said slidable bed in the direction of the optic axis of said first detecting system when a change-over of said first detecting system and said second detecting system is performed, wherein during the change-over from said first detecting system to said second detecting system, a predetermined optical member of said first detecting system is displaced from a position in the optical path of said first detecting system.

10. An ophthalmologic apparatus according to claim 9, wherein during the change-over from said first detecting system to said second detecting system, said detecting terminal is moved from a position rearward of said optical member to a position forward of said optical member.

11. An ophthalmologic apparatus according to claim 10, wherein said detecting terminal is moved only in the direction of the optic axis.

12. An ophthalmologic apparatus according to claim 10, wherein said detecting terminal is moved not only in the direction of the optic axis but also in a direction perpendicular to the optic axis.

13. An ophthalmologic apparatus according to claim 12, wherein said direction perpendicular to the optic axis is a vertical direction.

14. An ophthalmologic apparatus according to claim 10, wherein said detecting terminal is rotatably displaced about a predetermined point to thereby change over from said first detecting system to said second detecting system.

15. An ophthalmologic apparatus according to claim 10, wherein said optical member is an optical path deflecting member.

16. An ophthalmologic apparatus according to claim 10, wherein said optical member is an optical path deflecting member and an objective lens opposed to the eye to be examined.

17. An ophthalmologic apparatus comprising:

a first detecting system, disposed in a frame, for effecting a detection of first information of an eye to be examined at a predetermined working distance relative to the eye to be examined, the frame being supported by a slidable bed, said first detecting system effecting the detection of first information when the frame and the eye to be examined are aligned with each other by moving the slidable bed;

a second detecting system, disposed in the frame, for effecting the detection of second information of the eye to be examined with a detecting terminal thereof being brought into contact with the eye to be examined; and movable means for moving said detecting terminal of said second detecting system relative to the frame aligned with the eye to be examined in the direction of the optic axis of said first detecting system at least at positions directly before the eye to be examined without moving the slidable bed in the direction of the optic axis of the first detecting system when a change-over of said first detecting system and said second detecting system is performed, wherein said first information of the eye to be examined is cornea refractive power information and said second information of the eye to be examined is eye axis length information;

said first detecting system being provided with an index mark, an imaging optical system for receiving the corneal reflection light of said index mark, and image position detecting means for detecting the position of the corneal reflection image of said index mark with respect to said imaging optical system.

18. An ophthalmologic apparatus according to claim 17, wherein the detecting terminal of said second detecting system contains an ultrasonic wave transmitter and an ultrasonic wave receiver therein.

19. An ophthalmologic apparatus according to claim 17, provided with a front eye part observation system during the use of said first detecting system.

20. An ophthalmologic apparatus according to claim 17, provided with a front eye part observation system during the use of said second detecting system.

21. An ophthalmologic apparatus according to claim 17, provided with a front eye part observation system during the use of any of said first detecting system and said second detecting system.

22. An ophthalmologic apparatus according to claim 17, wherein said image position detecting means is connected to a front eye part observation monitor and is used not only for the detection of the position of the corneal reflection image but also for the observation of the front eye part.

23. An ophthalmologic apparatus according to claim 22, further provided with an observation optical system through which the front eye part of the eye to be examined around said detecting terminal can be observed with said detecting terminal being in contact with the eye to be examined.

24. An ophthalmologic apparatus according to claim 23, wherein said image position detecting means is provided on the image surface of said observation optical system, and during the use of any of said first detecting system and said second detecting system, the observation of the front eye part is possible through said common image position detecting means and said monitor.

25. An ophthalmologic apparatus according to claim 17, wherein during the change-over from said first detecting system to said second detecting system, a predetermined optical member of said first detecting system is displaced from a position in the optical path.

26. An ophthalmologic apparatus according to claim 25, wherein during the change-over from said first detecting system to said second detecting system, said detecting terminal is moved from a position rearward of said optical member to a position forward of said optical member.

27. An ophthalmologic apparatus according to claim 26, wherein said detecting terminal is moved only in the direction of the optic axis.

28. An ophthalmologic apparatus according to claim 26, wherein said detecting terminal is moved not only in the direction of the optic axis but also in a direction perpendicular to the optic axis.

29. An ophthalmologic apparatus according to claim 28, wherein said direction perpendicular to the optic axis is a vertical direction.

30. An ophthalmologic apparatus according to claim 26, wherein said detecting terminal is rotatively displaced about a predetermined point to thereby change over from said first detecting system to said second detecting system.

31. An ophthalmologic apparatus according to claim 26, wherein said optical member is an optical path deflecting member.

32. An ophthalmologic apparatus according to claim 26, wherein said optical member is an optical path deflecting member and an objective lens opposed to the eye to be examined.

33. An ophthalmologic apparatus according to claim 17, wherein said first detecting system is provided with an apertured mirror fixed in the optical path, and said detecting terminal is movable in the direction of the optic axis through the aperture of said apertured mirror.

34. An ophthalmologic apparatus according to claim 17, wherein said detecting terminal is biased toward the eye to be examined.

35. An ophthalmologic apparatus according to claim 17, further provided with an observation optical system through which the front eye part of the eye to be examined around said detecting terminal can be observed with said detecting terminal being in contact with the eye to be examined.

36. An ophthalmologic apparatus according to claim 35, wherein said observation optical system is provided with an optic axis forming a predetermined angle with respect to the direction of movement of said detecting terminal.

37. An ophthalmologic apparatus according to claim 35, wherein said observation optical system is provided with an optic axis coincide with the direction of movement of said detecting terminal.

38. An ophthalmologic apparatus according to claim 35, wherein said observation optical system and said first detecting system are provided with at least one common optical member.

39. An ophthalmologic apparatus according to claim 38, wherein said common optical member is a reflecting member, and the position of said reflecting member in said observation optical system is rotatively displaced relative to the position thereof in said first detection system.

40. An ophthalmologic apparatus, comprising:

a frame for detecting systems, said frame being supported by a slidable bed;

a first detecting system, disposed in said frame for effecting the detection of first information of an eye to be examined at a position being apart from the eye to be examined, said first detecting system effecting the detection of first information when said frame and the eye to be examined are aligned with each other by moving the slidable bed;

a second detecting system, disposed in said frame, said second detecting system including a detecting terminal for effecting the detection of second information of the eye to be examined brought into contact with the eye to be examined; and guiding means for guiding said detecting terminal to move relatively to said frame aligned with the eye to be examined in the direction of and apart from the eye to be examined without moving said slidable bed in the direction of and apart from the eye to be examined when a change-over of said first detecting system and said second detecting system is performed.

* * * * *

UNITED STATES PATENT AND TRADEMARK OFFICE
CERTIFICATE OF CORRECTION

PATENT NO. : 5,325,135
DATED : June 28, 1994
INVENTOR(S) : YUKITSUGU NAKAMURA, ET AL.

It is certified that error appears in the above-indentified patent and that said Letters Patent is hereby corrected as shown below:

On the title page:

Item: [63] RELATED U.S. APPLICATION DATA

"Nov. 19, 1989" should read --Nov. 2, 1989--.

[30] FOREIGN APPLICATION PRIORITY DATA

"051785" should read --62-51785--.
"Mar. 16, 1987 [JP] Japan 058286" should read
   --Mar. 13, 1987 [JP] Japan 62-58286--.
"135634" should read --62-135634--.
"135635" should read --62-135635--.

[56] REFERENCES CITED

U.S. PATENT DOCUMENTS

"3,070,997 1/1963 Papritz" should read
   --3,070,997 1/1963 Papritz, et al.--.

COLUMN 1

Line 26, "practiced" should read --practice--.

UNITED STATES PATENT AND TRADEMARK OFFICE
CERTIFICATE OF CORRECTION

PATENT NO. : 5,325,135
DATED : June 28, 1994
INVENTOR(S) : YUKITSUGU NAKAMURA, ET AL.

It is certified that error appears in the above-indentified patent and that said Letters Patent is hereby corrected as shown below:

COLUMN 3

Line 40, "So" should read --so--.

COLUMN 6

Line 56, "eve" should read --eye--.

COLUMN 12

Line 56, "coincide" should read --coincident--.

UNITED STATES PATENT AND TRADEMARK OFFICE
CERTIFICATE OF CORRECTION

PATENT NO. : 5,325,135
DATED : June 28, 1994
INVENTOR(S) : YUKITSUGU NAKAMURA, ET AL.

It is certified that error appears in the above-indentified patent and that said Letters Patent is hereby corrected as shown below:

COLUMN 14

Line 4, "relatively" should read --relative--.
   Line 7, "fromthe" should read --from the--.

Signed and Sealed this

Twenty-second Day of November, 1994

Attest:

BRUCE LEHMAN

Attesting Officer       Commissioner of Patents and Trademarks